US00PP29830P2

(12) United States Plant Patent
Ronald

(10) Patent No.: US PP29,830 P2
(45) Date of Patent: Nov. 13, 2018

(54) ***DASIPHORA* PLANT NAMED 'JEFMAN'**

(50) Latin Name: *Dasiphora fruticosa*
Varietal Denomination: Jefman

(71) Applicant: Jeffries Nurseries Ltd, Portage la Prairie (CA)

(72) Inventor: Wilbert Ronald, Portage la Prairie (CA)

(73) Assignee: JEFFRIES NURSERIES LTD, Portage la Prairie, Manitoba (CA)

( * ) Notice: Subject to any disclaimer, the term of this patent is extended or adjusted under 35 U.S.C. 154(b) by 0 days.

(21) Appl. No.: 15/731,355

(22) Filed: Jun. 1, 2017

(51) Int. Cl.
*A01H 5/02* (2018.01)

(52) U.S. Cl.
USPC ..... Plt./237

(58) Field of Classification Search
USPC ..... Plt./237
See application file for complete search history.

*Primary Examiner* — Anne Marie Grunberg
(74) *Attorney, Agent, or Firm* — Penny J. Aguirre

(57) ABSTRACT

A new cultivar of *Dasiphora fruticosa* plant named 'Jefman' that is characterized by its dense and rounded plant habit reaching 60 cm in height and width when mature, its flowers that open orange-red in color and slowly fade to orange and then yellow with good color rentention when grwon in full sun, its flowers that are single with 5 petals per flower, and its flower petals that overlap to create a fully round flower with no petal gaps.

2 Drawing Sheets

Botanical classification: *Dasiphora fruticosa.*
Variety denomination: 'Jefman'.

BACKGROUND OF THE INVENTION

The present invention relates to a new and distinct cultivar of *Dasiphora fruticosa* and will be referred to hereafter by its cultivar name, 'Jefman'. 'Jefman' is a new cultivar of hardy deciduous flowering shrub grown for use as an ornamental landscape plant.

'Jefman' arose from an on going breeding program conducted by the Inventor in Portage la Prairie, Manitoba, Canada. The objectives of the breeding program was to develop a cultivar of *Dasiphora* with more a compact plant habit, improved orange-red flower color and greater plant vigor.

'Jefman' originated from open pollination of *Dasiphora fruiticosa* 'Hinerob' (U.S. Plant Pat. No. 9,321) in 2006. The male parent is therfore unknown. The Inventor selected 'Jefman' as a single unique plant amongst the resulting seedlings in 2010.

Asexual propagation of the new cultivar was first accomplished by stem cuttings in June 2011 under the direction of the Inventor in Glenlea, Manitoba, Canada. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Jefman' as a unique cultivar of *Dasiphora.*

1. 'Jefman' exhibits a dense and rounded plant habit reaching 60 cm in height and width when mature.

2. 'Jefman' exhibits flowers that open orange-red in color and slowly fade to orange and then yellow with good color rentention when grwon in full sun.
3. 'Jefman' exhibits flowers that are single with 5 petals per flower.
4. 'Jefman' exhibits flower petals that overlap to create a fully round flower with no petal gaps.

The female parent of 'Jefman', 'Hinerob', differs from 'Jefman' in having flowers that are more red in color, wiry stems that require light pruning, a less dense plant habit, and a less vigorous grwith habit. The new *Dasiphora* can be most closely compared to the *Dasiphora fruticosa* cultivars 'UMan' (U.S. Plant Pat. No. 12,258) and 'Orange Whisper' (not patented). 'Uman' is similar to 'Jefman' in having dense foliage and a similar mature plant size. 'UMan' differs from 'Jefman' in having a mounded plant habit and in lacking color retention in full sun. 'Orange Whisper' is similar to 'Jefman' in having single flower that are orange in color. Orange Whisper' differs from 'Jefman' in having a slightly larger plant size at maturity and flower petals that do not overlap and are peach in color with dark orange brush marks at the base.

BRIEF DESCRIPTION OF THE DRAWINGS

The accompanying colored photographs illustrate the overall appearance and distinct characteristics of the new *Dasiphora*. The photographs were taken of a 5 year-old plant as grown outdoors at a nursery in Portage la Prairie, Manitoba, Canada.

The photograph in FIG. 1 provides a side view of a plant of 'Jefman' in bloom.

Figure 1:
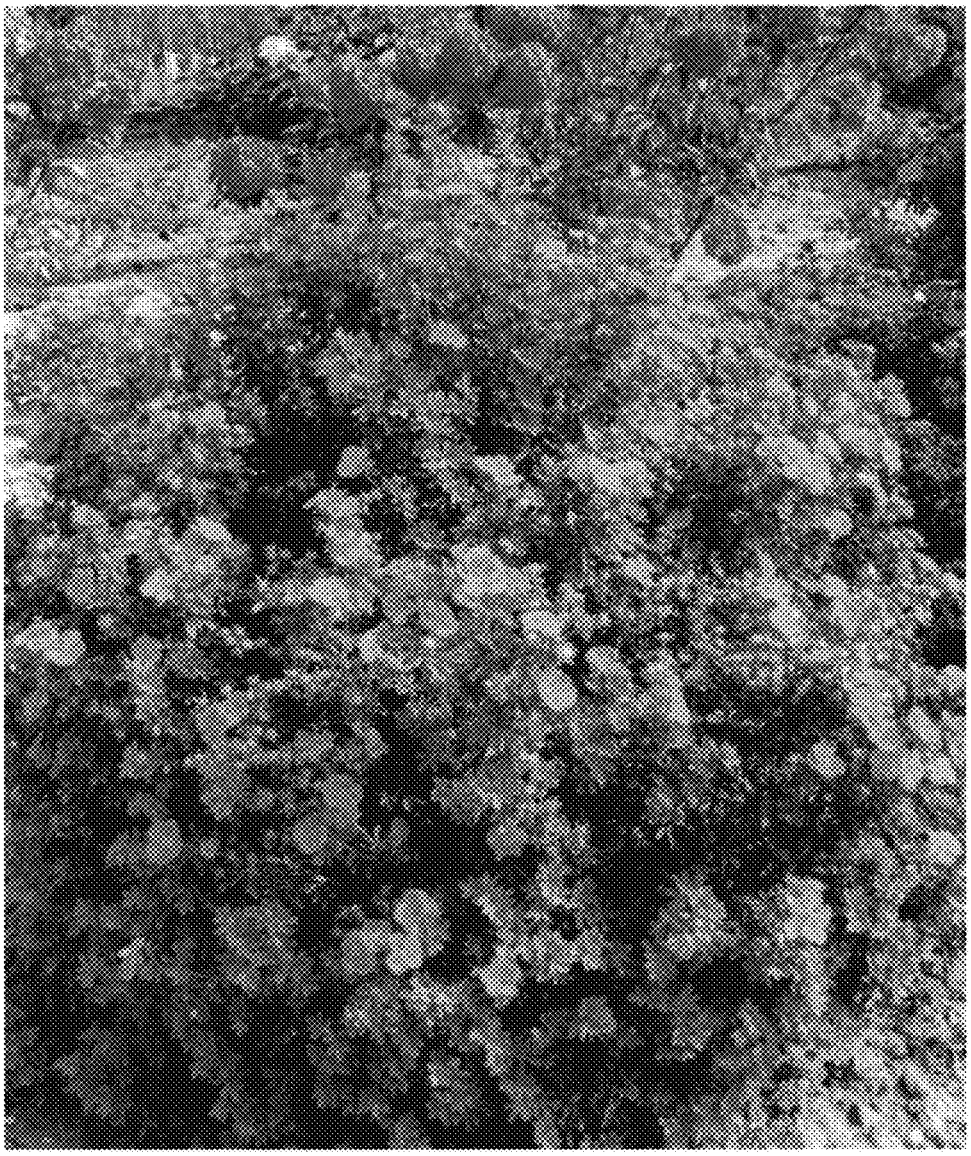
Figure 2:
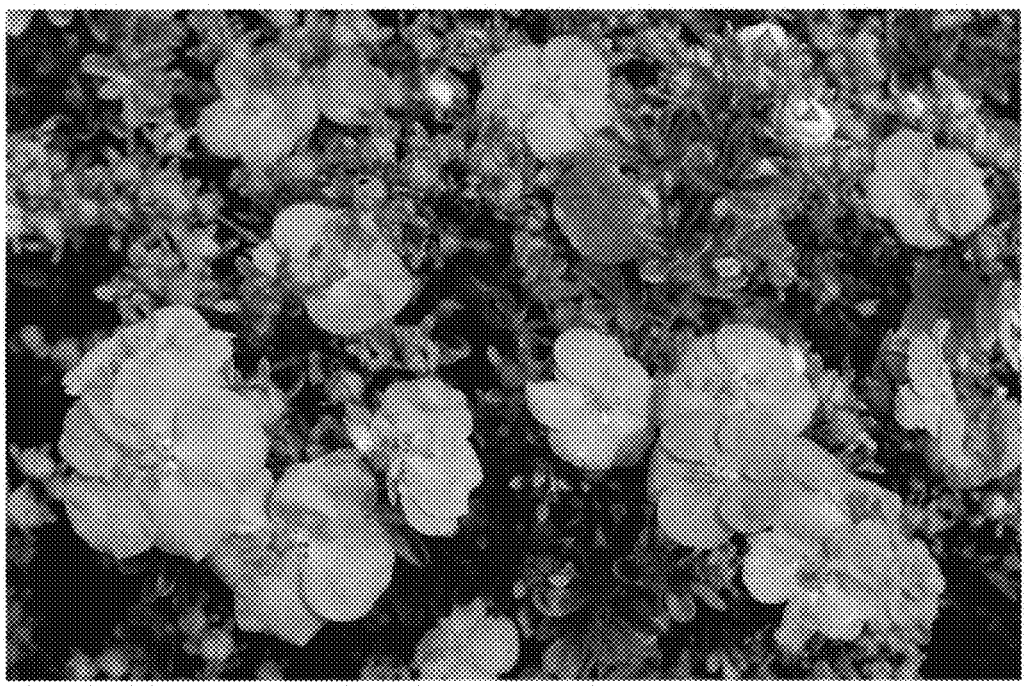

The photograph in FIG. 2 provides a close-up view of the flowers of 'Jefman'.

The colors in the photographs are as close as possible with the photographic and printing technology utilized and the color values cited in the detailed botanical description accurately describe the colors of the new *Dasiphora*.

DETAILED BOTANICAL DESCRIPTION

The following is a description of 2 year-old plants as grown outdoors in one-gallon containers in Portage la Prairie, Manitoba, Canada. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—Mid June to mid September in Canada.

*Plant type.*—Deciduous shrub.

*Plant habit.*—Compact, dense, rounded.

*Height and spread.*—An average of 60 cm in height and width when mature in the landscape.

*Cold hardiness.*—At least in U.S.D.A. Zone 2.

*Diseases.*—No resistance or susceptibility to diseases has been observed.

*Root description.*—Fibrous and dense, a blend of 158A and 161A in color.

*Propagation*—Stem cuttings.

*Growth rate.*—Moderate.

*Root development.*—Cuttings initiate roots in about 2 weeks and a fully rooted cutting is produces in about 6 weeks.

Branch description:

*Branch shape.*—Rounded.

*Branch color.*—Young; a blend of 145D, 199A and 142B, mature stems and oldest main branch; a blend of 175A, 201A and 199A.

*Branch surface.*—Young; shiny, tranluscent and densely to moderately covered with thin pilose hairs that match the surface color and are up to 1.5 mm in length, mature stems and oldest main branch; shiny and bark-like, exfoliating and waxy.

*Branching habit.*—Freely branching from the base.

*Branch size.*—Secondary branches; 19 cm in length, 3 mm in diameter, lateral branches; 10 cm in length, 3 mm in diameter, oldest main branch; 9 cm in length, 5 mm in diameter at the soil line.

*Branch quantity.*—An average of 10 lateral branches per main branch, up to 7 secondary branches per lateral branch.

*Branching strength.*—Mature and main branches are very strong, young branches are moderately strong.

Foliage description:

*Leaves.*—Compound, odd-pinnate division, alternate arrangement, triangular in shape, an average of 4 cm in length and 3 cm in width, internodes; an average of 1.5 cm in length.

*Leaflets.*—5, linear to spatulate in shape, acute to rounded apex, cuneate to acute base, color 137B on upper surface and 146B on lower surface, glabrous and matter upper and lower surface, veins are pinnate and inconspicuous, an average of 1.5 cm in length and 5 mm in width.

*Stipules.*—Double, a paper-like secondary stipule growing underneath main stipule and above the petiole, main stipule grows underneath the petiole and over the paper-like stipule, seconday stipule; elliptic to lanceolate in shape, an average of 6 mm in length and 4 mm in width, transluscent, inner and outer surface color 165A, inner and outer surface slightly thin and matte, main stipule; elliptic to lanceolate in shape, an average of 3 mm in length and 2 mm in width, inner and outer surface is glossy and pilose, 145A in color.

*Petioles.*—Petioles; an average of 4.5 cm in length and 1 mm in diameter, moderate strength, color 193B, surface is pilose and slightly glossy, petiolules; none.

Inflorescence description:

*Inflorescence type.*—Solitary, axillary at the apex of stems.

*Flower number.*—An average of 2 to 6 per stem open at one time.

*Flower fragrance.*—None.

*Flower longevity.*—About 5 days, self-cleaning.

*Flower type.*—Single.

*Flower aspect.*—Upward to slightly outward.

*Flower size.*—An average of 4 cm in diameter and 5 mm in depth.

*Peduncles.*—An average of 1.5 cm in length and 1 mm in diameter, 144A to 144B with flushes of 173A in color, densely pubescent surface with hairs up to 1 mm in length that match surface color, moderately strong.

*Pedicels.*—An average of 1 cm in length and 0.5 mm in diameter, 144A to 144B with flushes of 173A in color, densely pubescent surface with hairs up to 1 mm in length that match surface color, moderately strong.

*Flower buds.*—Flattened globose in shape, an average of 7 mm in diameter and 6 mm in depth prior to opening, 145A in color with very light flushes of 184A.

*Sepals.*—5, ovate in shape, entire margin, color on upper and lowers surface; 145A with small and faint flushes of 166B, an average of 8 mm in length and 5 mm in width, acuminate apex, truncate base, slightly pubescent on upper and lower surface, epicalyx; 5-lobed, lanceolate to oblanceolate in shape, entire margin, acute to bluntly acute apex, an average of 7 mm in length and 4 mm in width, upper and lower surface; 143A in color and very slightly pubescent.

*Petals.*—5 per flower, self-cleaning, oval-rounded in shape, smooth and matte upper and lower surface, entire margins, truncate base, rounded apex, an average of 1.5 cm in length and width, color; when opening upper surface a blend of N34A, N25A and 20A, fully open upper surface N25A, base and mid-section 15A, when opening lower surface 11B, fully open lower surface 20A.

*Receptacle.*—Very densely pubescent, 2 mm in depth, 5 mm in diameter, 144A in color.

Reproductive organs:

*Pistils.*—Average of 60, en masse 4 mm in diameter, stigma; very minute, rounded in shape and less than 0.5 mm in diameter, 19A in color, style; average of 3 mm in length and <0.5 mm in width, color 19A at the top section and NN155D at the mid section to base, ovary; superior, 4 mm in diameter and depth, 144A in color.

*Stamens.*—24 per flower, filaments; average of 3 mm in length and 13C in color, anthers; average of 1 mm in length and 0.5 mm in width, ovate in shape, center is 13C in color, outer margins are 177A in color, pollen; too minimal in quantity to record color.

*Fruit and seed.*—Has not been observed to date.

It is claimed:

1. A new and distinct cultivar of *Dasiphora* plant named 'Jefman' as herein illustrated and described.

* * * * *